United States Patent [19]

Peters

[11] Patent Number: 5,188,585
[45] Date of Patent: Feb. 23, 1993

[54] LUMBO-SACRAL ORTHOPEDIC SUPPORT
[75] Inventor: Helena Peters, Bromma, Sweden
[73] Assignee: Camp International, Inc., Jackson, Mich.
[21] Appl. No.: 692,111
[22] Filed: Apr. 26, 1991
[51] Int. Cl.⁵ ............................................. A61F 5/00
[52] U.S. Cl. ...................................... 602/19; 2/311; 128/100.1
[58] Field of Search ................. 602/19; 128/96.1, 99.1, 128/100.1, 101.1, 106.1, 107.1; 2/255, 311, 319, 235-237

[56] References Cited
U.S. PATENT DOCUMENTS

| | | | |
|---|---|---|---|
| 1,201,933 | 10/1916 | Burk | 128/96.1 X |
| 2,117,309 | 5/1938 | Fritsch | |
| 2,362,402 | 1/1968 | Loeffel et al. | |
| 3,282,264 | 11/1966 | Connelly | |
| 3,351,053 | 11/1967 | Stuttle | |
| 3,577,986 | 5/1971 | Regent | 128/107.1 X |
| 3,717,143 | 2/1973 | Johnson | |
| 3,754,549 | 8/1973 | Nelkin | 128/100.1 |
| 3,804,084 | 4/1974 | Lehman | 602/26 |
| 3,888,245 | 6/1975 | Berntson et al. | |
| 3,920,008 | 11/1975 | Lehman | |
| 3,927,665 | 12/1975 | Wax | |
| 4,022,197 | 5/1977 | Castiglia | |
| 4,175,553 | 11/1979 | Rosenberg | |
| 4,245,628 | 1/1981 | Eichler | 602/19 |
| 4,836,194 | 6/1989 | Sebastian et al. | 602/19 |
| 4,991,234 | 2/1991 | Greenberg | 602/19 X |
| 5,040,524 | 8/1991 | Votel et al. | 602/19 |
| 5,086,759 | 2/1992 | Buddingh | 128/101.1 X |

Primary Examiner—Richard J. Apley
Assistant Examiner—Linda C. M. Dvorak
Attorney, Agent, or Firm—Price, Heneveld, Cooper, DeWitt & Litton

[57] ABSTRACT

A lumbo-sacral support formed by the combination of a lumbo-sacral belt adapted to encircle the torso of the wearer and a separate, releasable, fastenable compression belt which can be infinitely positioned vertically or horizontally across the lower back and lumbar regions of the wearer. In a more specific aspect, a lumbar pad is used in combination with the primary belt and compression belt.

21 Claims, 2 Drawing Sheets

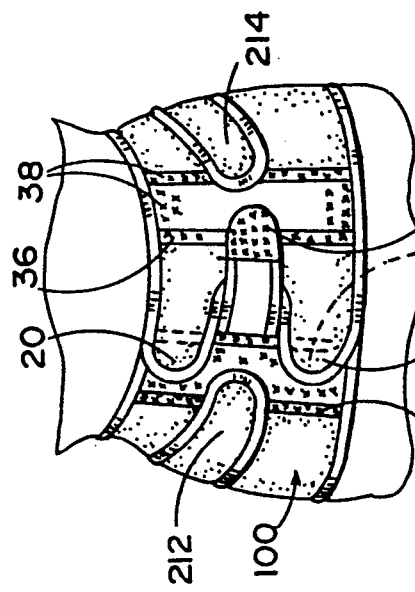
FIG. 1
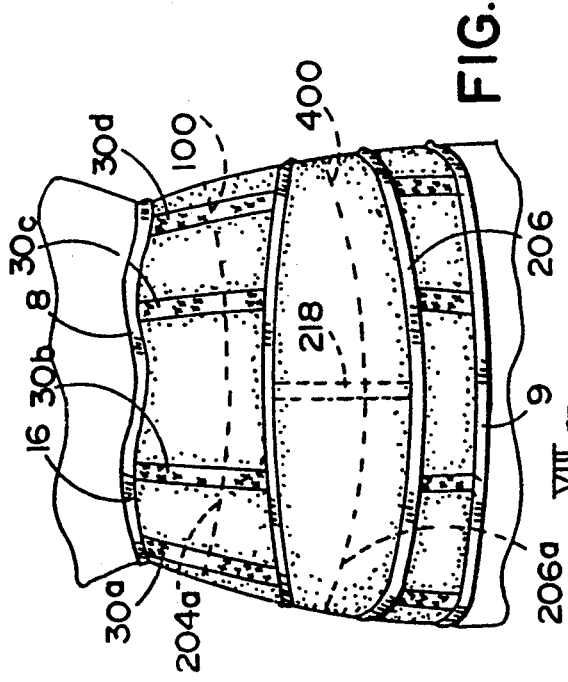
FIG. 2
FIG. 3

LUMBO-SACRAL ORTHOPEDIC SUPPORT

BACKGROUND OF THE INVENTION

This invention relates to ready-to-wear orthotic supports and, particularly, to orthopedic garments of the torso encircling-type, for providing lumbo-sacral support.

A wide variety of lumbo-sacral support constructions are known. The supports should be capable of providing controlled circumferential compression to the lumbar, sacral and abdominal regions to lift and compress the abdomen while stabilizing lumbar and sacral muscles and ligaments, decreasing ligamentous and muscular stress on and compression of the vertebrae, and assisting in positioning the pelvis in a position of pelvic tilt.

All back problems are or at least have the potential to be serious. Back supports can basically be divided into three categories, rigid supports such as Knight Taylor braces and body jackets; semi-rigid supports usually made of a non-stretch canvas-type fabric which include rigid shaped steels; and firm supports made of flexible resilient materials which may or may not include shaped steels or plastic stays and are usually provided with releasable hook and loop fastening means. The type of support prescribed or recommended for a patient may take many factors into consideration: diagnosis, age, physical condition, tolerance to bracing, lifestyle, etc. For example, in the United States, an L1 fracture in a young person may only require a Firm Support because they heal fast and are not so prone to falling, while for the same diagnosis probably a semi-rigid or even rigid brace would be recommended for an older person as it is going to take longer for the fracture to heal and there is a higher incidence of falling.

Firm supports are also known as soft goods garments and include one-piece, two-way stretch girdles intended to improve posture and the like. Others have elaborate panel and strap arrangements to pull in abdomen and buttocks areas, support sagging muscles, and the like. Quite often, firm support garments are uncomfortable to wear, apply pressure at unnecessary places and do not provide sufficient pressure at desired parts of the anatomy. Adjustment of many soft good garments for tensioning, shape and support are often inconvenient, or not wholly effective.

Among the more simple lumbo-sacral support devices are those disclosed in U.S. Pat. Nos. 4,175,553 and 3,717,143. The orthopedic garment disclosed in U.S. Pat. No. 4,175,553 includes a removable lumbo-sacral-orthosis which cannot, however, be positioned at a desired region of the pain unless the pain occurs in that portion of the back directly under the removable orthosis. In addition, there is no provision for providing additional compression except through the use of the lumbo-sacral-orthosis. The orthopedic garment in U.S. Pat. No. 3,717,143 includes vertical stays which are bent to conform to the wearer's lower torso and two straps which are fixedly attached to the garment at the top and bottom edges. The straps are provided to firmly secure the corset at the proper place about the lower part of the torso.

SUMMARY OF THE INVENTION

In accordance with the present invention, there is provided an orthotic support for therapeutic use in the lumbo-sacral region for alleviating pain resulting from injury, for preventing injury, to improve posture and to support sagging or weak muscles. The lumbo-sacral support of the present invention comprises the combination of a primary, body-encircling, lumbo-sacral belt and a detachable, variably positionable compression belt or cinch strap which can be positioned anywhere between the upper and lower edges of the primary belt so that additional compression can be exerted at selected portions of the lumbar and/or sacrum areas of the back.

This provides a means for the compression belt to be variably positionable on the primary belt to direct compression more precisely to the area of pain. It also provides the primary belt with a reasonable amount of girth adjustment. The belts conform well to the anatomy, allowing compression to be applied where most needed and reduce edema while providing good support without excessive bulk. The therapeutic back supports of this invention provide relief from pain and stabilization of muscles in the lumbar region.

BRIEF DESCRIPTION OF THE DRAWINGS

The objects and advantages of the present invention will be more readily appreciated from the following description and accompanying drawings wherein:

FIG. 1 is an elevational view of the two-piece lumbo-sacral support as viewed on a person from the rear;

FIG. 2 is a front-elevational view of the support of FIG. 1;

FIG. 3 is a plan view of one of the elements of the support;

DESCRIPTION OF THE PREFERRED EMBODIMENTS

Figure 6:
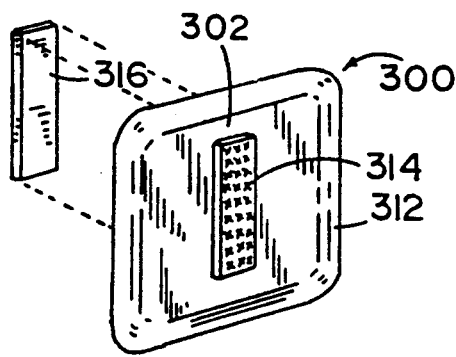
FIG. 6 is a perspective view of a lumbar pad that can be used in combination with the two elements of FIGS. 3 and 4.
Figure 7:
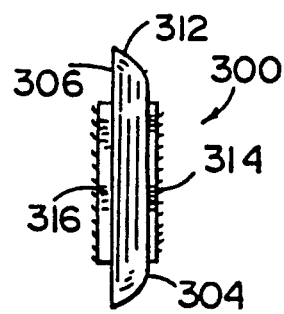
FIG. 7 is an elevated side view of the lumbar pad of FIG. 6.
Figure 4:
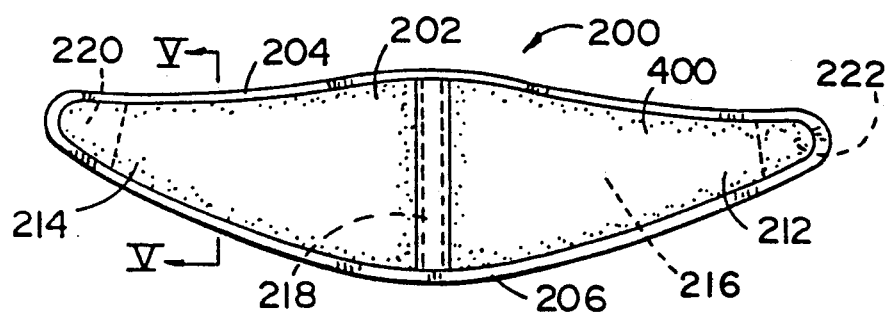
FIG. 4 is a plan view of the second element of the support.

The lumbo-sacral back support, secondary compression or cinch belt are formed from a resilient flexible material comprising an exposed outer surface or layer and an inner layer or surface adapted to be worn next to the body area. More particularly, the supports of this invention can be formed from substantially any natural or synthetic material, including both inelastic and elastic materials, having sufficient flexibility and resiliency to enable the support to anatomically conform to the body member to which it is applied. In addition, the supports include mutually intercooperating connector means comprising loop keeper means on at least a portion of the outer surface of the support and a companionate array of hook keeper means on at least a portion of the inner surface of the support which confront the loop keeper means when both keeper means are in an overlying relationship on the supports; the hook means being adapted in response to pressure against the loop means to intermesh with the loop means and releasably cling to the loop means, to be separated therefrom in response to a peeling quick yanking force.

The resilient flexible natural or synthetic materials suitable for use in the practice of the invention include fabrics made from inelastic fibers such as nylon fibers, polyester fibers, cotton fibers and the like; elastomers such as natural rubber, neoprene rubber and the like; and elasticized fibers comprising a blend of at least one inelastic fiber, such as nylon, polyester, cotton and the like and at least one elastomeric fiber, such as those sold under the trademark Lycra, and including combinations of two or more natural and/or synthetic materials, generally in the form of a laminated structure.

The preferred material comprises a flexible resilient elasticized fabric laminate comprising an outer elasticized fabric layer, an open-cell polymeric foam core and an inner or proximal elasticized fabric layer. The foam core is coextensive with and adhered to both inner and outer layers. The laminate is stretchable in all directions. The inner and outer layers comprise elasticized fabrics having substantially the same degree of stretch in all directions. The outer elasticized fabric layer is preferably a high moisture absorbent fabric comprising a blend of at least one inelastic fiber and at least one elastic fiber, with a blend of inelastic polyamide and elastic polyurethane being currently preferred. The outer surface has a brushed felt-like texture comprising myriad upstanding and relatively free fiber loop fastening means. The inner layer is preferably a lower moisture absorbent but good wicking fabric comprising an elasticized cotton fabric comprising a blend of cotton and at least one elastic fiber, preferably an elastic polyurethane fiber. The polymeric foam core is an open-celled cellular material which is preferably a polyurethane or polystyrene foam and is most preferably a polyethylene foam. Currently, a preferred composite comprises 35 weight percent polyamide, 42 weight percent cotton, 18 weight percent polyurethane elastic fiber and 5 weight percent open-cell polyethylene foam, based on total weight of the composite. The provision of elasticized fibers and fabrics from different natural and synthetic fibers is well-known in the art, and there is no need for elaboration. The composite is lightweight, stretchable to anatomically conform to the body member, durable and easily laundered in home washing machines. Drip-drying is the preferred method of drying laundered supports. The high-absorbent elasticized outer layer, the open-cell polymeric foam core and the low-absorbent elasticized inner layer cooperatively provide a breathable composite which aids in the transfer of moisture, such as perspiration from the wearer's body to the outer surface of the outer or exposed layer, which has sufficient porosity to enable moisture to be wicked from the body to the outer surface of the support. The elasticized cotton inner layer ensures dryness, provides a comfortable feel against the body and a feeling of soothing warmth for injured and arthritic joints when engaging in strenuous activities while minimizing heat buildup during such activities.

The lumbo-sacral support of this invention comprises the combination of a lumbo-sacral belt 100 adapted to encircle the torso of the wearer and a separate releasably fastenable lumbo-sacral compression belt 200 which is infinitely positionable vertically across the lower back and lumbar regions of the wearer and is adapted to partially encircle the torso. More particularly, the lumbo-sacral belt 100, adapted to the circular torso of the wearer, comprises a unitary fabric composite which is stretchable in all directions. The longitudinal length of the compression belt is somewhat shorter than the longitudinal length of the primary belt and is typically sized to surround the lumbar region and encircle the hips of the wearer.

A lumbar support pad 300 may be employed in the practice of the invention. It preferably comprises a polymeric foam pad of rectangular configuration and is equipped with loop and hook fastening means on both faces, so that the pad can be releasably attached to the outer surface of the primary lumbo-sacral belt 100 and the inner surface or liner of the secondary compression belt 200. In most cases, such as an extreme lordosis condition, or bad posture, the pad will be placed at the small of the back and will be attached to both primary and secondary belts by means of the centrally-located loop and hook fastening means feature incorporated into each belt.

The primary and secondary belts are preferably formed from one-piece elasticized laminates comprising an outer elasticized fiber layer 2, a polymeric open-cell foam center 4 and an elasticized inner fiber layer or liner 6, with the foam center 4 being adhered to both inner and outer layers 2 and 6 and with the preferred edges being covered by a stitched elasticized piping. The laminate is stretchable in all directions. The inner and outer layers 2 and 6 comprise elasticized fabrics having substantially the same degree of stretch in all directions. The entire outer elasticized fabric layer comprises fastening looped fibers having a soft-brushed appearance with polyamide looped fibers being currently preferred. The inner layer comprises an elasticized cotton fabric. The open-cell foam core is flexible and can be made from any foamable natural or synthetic resin with an elastomeric polyurethane foam core being currently preferred. The providing of elasticized fibers from different natural or synthetic fibers is well-known in the art, and there is no need for elaboration. Currently, a satisfactory composite comprises 35 weight percent polyamide looped fiber, 42 weight percent cotton, 18 weight percent elastomeric polyurethane fiber, which is available under the trademark Lycra and 5 weight percent of polyethylene foam, based on total weight of elasticized laminate.

With reference to FIGS. 1–4, the orthotic support of this invention comprises the combination of a primary lumbo-sacral band generally indicated at 100 and a secondary compression band generally indicated at 200. The compression band 200 is adapted to be infinitely positioned and attached to the outer surface of primary support band 100. The support band may optionally include a lumbar pad generally designated at 300 which is adapted to be selectively positioned between the outer surface of the primary band and the inner surface of the compression band.

Figure 5:
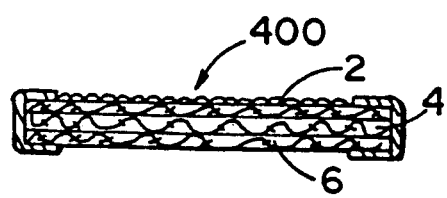
FIG. 5 is a cross-sectional view of the material from which the two elements are constructed taken along the plane V—V of FIG. 4.

Both the primary band 100 and the secondary compression band 200 are formed of a laminated elasticized fabric material 400 (FIG. 5) comprising an outer fabric 2, an inner fabric 6 and a polymeric open-cell foam core 4 disposed between fabric layers 2 and 6 and integrally adhered thereto.

Primary lumbo-sacral band 100 is preferably formed of a unitary elongated elasticized material 400 as shown on FIG. 3 having an upper edge 8 extending along a substantially straight line; a lower edge 9 and ends 10 and 12. The upper and lower edges define a central region 18 having an increased vertical dimension or width defining a lumbar skirt. The lower edge includes tapered end portions 9a and 9b which taper upwardly from the central portion 9c forming the lumbar skirt.

Figure 8:
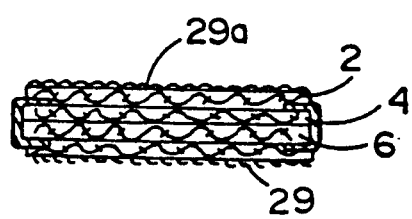
FIG. 8 is a cross-sectional view taken along the plane VIII—VIII of FIG. 3.

End portions 9a and 9b merge into end regions 12 and 10, respectively. The end 12 is shaped to provide the integral C-shaped tabs 20 and 22 to define a recess 24 medially located therebetween. End region 10 terminates in a substantially straight edge 26 and is provided with a tab 27 which is fixedly attached at its end 28 by sewing to end region 10 a distance spaced from the edge 26. This distance is substantially equal to the depth of recess 24. Tab 27 is adapted to mate into recess 24 and pass beyond for engagement with the outer surface 2 of band 100, thereby providing for some degree of girth adjustment. The inner faces of tabs 20, 22 and 28 are provided with hook type fastening means 21, 23 and 29 for engagement with the hook type fabric of surface 2. It also has a loop type fabric 29a on its outer surface (FIG. 8) in the event the hook type fastening means of the compression belt 200 overlaps it. A plurality of vertical pockets 30a, 30b, 30c and 30d are sewn in the garment within the area defined by center region (lumbar skirt) 18 for receiving flexible stays 32 (shown in pocket 30a) as is conventional in garments of this type. The stays have a substantially perfect memory, that is, capable of bending to conform to the torso and the applied compressive pressure when the secondary compression belt 200 is attached to the primary belt 100 and returning to a substantially flat configuration when the pressure is released.

The horizontal width of the lumbar skirt region is sufficient to overlie the wearer's back. End regions 10 and 12 are provided with pockets 36 and 37 for receiving stays such as 32a which aid in preventing roll-up of a garment when in use. Pockets 36 and 37 are formed by elasticized fabric comprising a myriad of loops which provide a stronger holding power than the loop surface of material 400. End portions 10 and 12 also include vertical loop fastener strips 38 and 39 which provide a point of attachment for C-shaped tabs 20, 22 and 28 and the ends of compression belt 200. The entire periphery of band 100 is reinforced with an elasticized piping or binding 16 which is stitched around the entire periphery of band 100.

Secondary compression belt 200 is formed from the same elasticized fabric composite 400 as is belt 100 and includes an enlarged center portion 202 defined by upper edge 204 and lower edge 206, which converge to merge into end portions 212 and 214. The inner surface 216 of band 200 is provided with a vertically-oriented hook fastener strip 218 having hooked attachments for engagement with the outer surface 34 of band 100. End portions 212 and 214 are provided on the inner face 216 of band 200 with hook attachment means 220 and 222 for engagement with the outer surface to band 100.

Lumbar pad 300 (FIG. 6) includes a generally rectangular-shaped polymeric foam body 302 having a bottom face 306, a top face 304 and side edges 312. Top face 304 merges radially downward into side edges 312 to provide a gently rounded contour. Lumbar pad 300 is provided with loop/hook strips 314 and 316 on the top and bottom faces, respectively, for engagement preferable with outer surface 2 of pad 100 and hook fastener strip 218 of compression belt 200.

It will be appreciated that the lumbo-sacral support hereinbefore described may be readily applied about the lower torso of the patient. Particularly, the lumbar skirt region 14 may be disposed about the patient's lumbar region with layer 6 adjacent the patient's body with end portions 10 and 12 being wrapped about the side and abdominal regions and joined one to the other by pressing the inner hook fastening faces of tabs 20, 22 and 27 against the loop fastening strips 36, 37, 38, and 39 or outer fabric 2. The lateral extent of the free end of tab 27 provides a degree of adjustability when initially securing the support about the torso. When belt 100 is wrapped in proper position, compression belt 200 is located where needed in the lumbar region of belt 100 and attached to the loop fastening surface 2 of belt 100 and is, likewise, pulled about the torso and attached through the hook attachments 20 and 222 to the looped fabric surface 2 of belt 100 to provide the desired degree of compression. In this manner, lumbo-sacral belt 100 contours the buttocks to ensure an anatomical fit. The secondary compression belt 200 bears against the lumbo-sacral region and forces the flexible stays 32 to conform with the body contour to provide a desired degree of compression. The stays 32 will limitedly flex when the patient sits or bends or engages in other physical activities. In addition, the stays 36 in combination with the location of tabs 20, 22 and 27 in combination with compression belt 200 preclude rolling of the edges.

The compression pad can be adjusted to an infinite number of vertical positions. FIG. 1 illustrates only one position, it being understood that it can be adjusted to any position such as illustrated by the phantom lines 204a and 206a.

It will be appreciated that the lumbo-sacral support of this invention can be provided in various sizes, depending upon the size of the patient undergoing treatment. It will also be appreciated that the combination of the lumbo-sacral belt 100 and the compression belt 200 provide a substantially comfortable fit about the patient. The adjustability of the lumbar pad permits positioning where needed for pain relief or lordosis support and the integral front closure straps provide ease of application. In addition, the elasticized fabric laminate provides a breathable effect whereby moisture, such as perspiration, can be wicked from the patient's skin and transferred to the surface where it is evaporated. The foregoing described support is fabricated from a single piece of laminated fabric in a ready and easy manner chiefly by a cutting, stitching or sewing operation. The essentially seamless character of both belts also enhances the comfort of the wearer.

The invention may be embodied in other specific forms without departing from the spirit or essential characteristics thereof. The present embodiment is, therefore, to be considered in all respects as illustrative and not restrictive, the scope of the invention being indicated by the appendant claims added in by the foregoing description, and all changes which come within the meaning and range of equivalency of the claims are, therefore, intended to braced therein.

The embodiments of the invention in which an exclusive property or privilege is claimed are define as follows:

1. A lumbo-sacral orthopedic device adapted to encircle the torso comprising, in combination:
   a flexible, resilient, primary band member having an intermediate region having upper and lower edges defining therebetween an intermediate section of said band that is of sufficient width and composition to provide support to the back in the lumbar and sacrum areas of the back, said primary band member having end portions that extend in opposite direction about the torso, and overlap attaching means on the overlapping end portions for adjustably attaching said ends together for accommodating torsos of different girth dimensions;

a compression band formed of a flexible, resilient material and of substantially less width than the said width of said intermediate section of said primary band member; said compression band being of sufficient length to provide ends which extend at least from the back to the front of the torso, means for securing the ends at the front of the torso;

means for causing said compression band, when extended from the back to the front of the torso ad secured at the front of the torso, to exert increased compression said primary band member, such compression being transmitted to predetermined areas of the back;

said compression band being vertically movable relative to said intermediate region of said primary band member to different positions between said upper and lower edges of said primary band member whereby compression of said primary band member on selected areas of the back in the lumbar or sacrum areas can be selectively increased by said compression band.

2. A lumbo-sacral orthopedic device adapted to encircle the torso comprising, in combination:

A flexible, stretchable, primary band member having an intermediate region having upper and lower edges defining therebetween an intermediate section of said band that is of sufficient width and composition to provide support to the back in the lumbar and sacrum areas of the back, said primary band member having end portions that extend in opposite directions about the torso, and overlap attaching means on said overlapping end portions for adjustably attaching said ends together for accommodating torsos of different girth dimensions;

a compression band formed of a flexible, stretchable material and of substantially less width than the said width of said intermediate section of said primary band member; said compression band being of sufficient length to provide ends which extend at least from the back to the front of the torso, means for securing the ends at the front of the torso;

means for causing said compression band, when extended from the back to the front of the torso and secured at the front of the torso, to exert increased compression on said primary band member, such compression being transmitted to predetermined areas of the back;

said compression band being vertically movable relative to said intermediate region of said primary band member to different positions between said upper and lower edges of said primary band member whereby compression of said primary band member on selected areas of the back in the lumbar of sacrum areas can be selectively increased by said compression band.

3. The device of claim 2 in which the outer surface of said primary band member and said end portions of said compression band have cooperable releasable fastening means whereby the engagement of said end portions with said outer surface of said primary band member fastens said compression band to said primary band member.

4. The device of claim 2 in which said intermediate region of said primary band member defines a lumbar skirt; said end portions being of reduced width and adapted to extend about the lumbar sacral area and overlie the abdominal regions; said primary band member having lateral sides tapering upwardly from said lumbar skirt to merge into said reduced end portions, one of said reduced end portions including upper and lower releasable fastening means, said upper and lower releasable fastening means defining a C-shaped opening therebetween, the other reduced end portion being provided with medially-located releasable fastening means dimensioned to be received within the C-shaped recess of its opposite end, and adapted to extend beyond the C-shaped recess.

5. The device of claim 4 in which the outer surface of said primary band member and said end portions of said compression band have cooperable releasable fastening means whereby the engagement of said end portions with said outer surface of said primary band member fastens said compression band to said primary band member.

6. The device of claim 3 in which said intermediate region of said primary band member includes a plurality of sewn-in pockets, each pocket containing a flexible stay, said pockets being vertically-oriented, said outer surface of said primary band member including a looped fastener material and said ends of said compression band including interlockable hooked fastener material thereby providing means for connecting said ends of said compression band to the outer surface of said primary band member.

7. The device of claim 2 in which the outer surface of said primary band member and said inner surfaces of the ends of said primary band member have cooperable releasable fastening means whereby the engagement of the inner surfaces of said ends of said primary band with said outer surface of the ends of said primary band member fastens said ends together.

8. The device of claim 2 wherein said intermediate region of said primary band member includes a plurality of sewn-in pockets, each pocket containing a flexible stay, said pockets being vertically-oriented, said outer surface of said primary band member in said intermediate section including a looped fastener material.

9. The device of claim 7 wherein said ends further include vertically-oriented strips extending from the top edge to the bottom edge of said ends and providing a releasable fastening means.

10. The device of claim 2 in which the compression band has an enlarged width intermediate portion and reduced width end portions which terminate in releasable fastening means.

11. A lumbo-sacral orthotic support adapted to encircle the torso comprising, in combination, an elongated, unitary, flexible, primary band member and a compression band; said primary band member comprising a laminated, elasticized material, said primary band member including an intermediate region of substantial width to cover at least portions of the lumbar and sacrum areas of the back; said intermediate region of said primary band member defining a lumbar skirt; said primary band member having end portions being of reduced width and adapted to extend about the lumbar sacral area an overlie the abdominal regions; said primary band member having lateral sides tapering upwardly from said lumbar skirt to merge into said reduced end portions, one of said reduced end portions including upper and lower releasable fastening means, said upper and lower releasable fastening means being spaced a first distance from one another to define, with said primary band member, a C-shaped recess therebetween, the other reduced end portion having a width less than said first distance between said upper and said lower releasable fastening means and said other reduced end portion being adapted to be matingly received within and extend beyond said C-shaped recess;

said compression band comprising a releasably fastenable band having an enlarged intermediate portion and reduced end portions which terminate in releasable fastening means for engagement with and attachment to the outer surface of said primary band member.

12. A lumbo-sacral orthotic support in accordance with claim 11 wherein said primary band member and said compression band are formed from an elasticized fabric laminate including an outer surface comprising an elasticized fabric, the entire surface of which is provided with fastening loops, an elasticized cotton fabric inner layer and a polymeric open-cell foam body disposed between said outer layers and said inner layer and integrally bonded thereto.

13. A lumbo-sacral orthotic support in accordance with claim 12 wherein said intermediate region of said primary band member includes a plurality of sewn-in pockets, each pocket containing a flexible stay, said pockets being vertically-oriented, said outer surface of said primary band member including a looped fastener material.

14. A lumbo-sacral orthotic support in accordance with claim 11 wherein said primary band member and said compression band are formed from an elasticized fabric laminate including an outer surface comprising an elasticized fabric, the entire surface of which is provided with fastening loops, said releasable fastening means on the reduced end portions of said compression band including fastening hooks.

15. A lumbo-sacral orthotic support in accordance with claim 13 wherein said end regions include at least one sewn-in pocket containing a flexible stay.

16. A lumbo-sacral orthotic support in accordance with claim 2 including a lumbar support pad, disposed between said primary band member and said compression band and adapted to be releasably attached to one of the outer surface of said first flexible band or the inner surface of said compression band.

17. The device of claim 6 in which said sewn-in pockets are formed by a material of the loop type.

18. The device of claim 7 in which the releasable fastening means on the outer surface of said primary band member is at least one strip of material; and one of said fastening means on said strip and said fastening means on the inner surface of said ends is a material of the loop type and the other of said releasable fastening means is a material of the hook type.

19. A lumbo-sacral orthotic support adapted to encircle the torso comprising, in combination, an elongated, unitary, flexible, primary band member and a compression band; said primary band member comprising a laminated, elasticized material, said primary band member including an intermediate region of substantial width to cover at least portion of the lumbar and sacrum areas of the back; said intermediate region of said primary band member defining a lumbar skirt; said band member having end portions being of reduced width and adapted to extend about the lumbar sacral area and overlie the abdominal regions; said primary band member having lateral sides tapering upwardly from said lumbar skirt to merge into said reduced end portions, means for attaching said end portions together at the abdominal region;

said compression band comprising a releasably fastenable, vertically positionable band having an enlarged intermediate portion and reduced end portions which terminate in releasable fastening means for engagement with and attachment to the outer surface of said primary band wherein said intermediate portion of said compression band is vertically positionable relative to said intermediate region of said primary band member.

20. A lumbo-sacral orthotic support in accordance with claim 19 wherein said primary band member and said compression band are formed from an elasticized fabric laminate including an outer surface comprising an elasticized fabric, the entire surface of which is provided with fastening loops, said releasable fastening means on the reduced end portions of said compression band including fastening hooks.

21. A lumbo-sacral orthotic support in accordance with claim 19 including a lumbar support pad, disposed between said primary band member and said compression band and adapted to be releasably attached to one of the outer surface of said first flexible band or the inner surface of said compression band.

* * * * *

UNITED STATES PATENT AND TRADEMARK OFFICE
CERTIFICATE OF CORRECTION

PATENT NO. : 5,188,585
DATED : February 23, 1993
INVENTOR(S) : Helena Peters

It is certified that error appears in the above-indentified patent and that said Letters Patent is hereby corrected as shown below:

Column 7, line 11:
    "torso ad" should be --torso and--.

Column 7, line 13:
    After "compression" insert --on--.

Column 7, line 56:
    "of sacrum" should be --or sacrum--.

Column 8, line 61;
    "an overlie" should be --and overlie--.

Column 10, line 14:
    "portion" should be --portions--.

Signed and Sealed this

Seventh Day of March, 1995

Attest:

BRUCE LEHMAN

*Attesting Officer*      *Commissioner of Patents and Trademarks*